United States Patent [19]
Bradley et al.

[11] Patent Number: 6,048,695
[45] Date of Patent: Apr. 11, 2000

[54] CHEMICALLY MODIFIED NUCLEIC ACIDS AND METHODS FOR COUPLING NUCLEIC ACIDS TO SOLID SUPPORT

[75] Inventors: Allan Bradley; Wei Wen Cai, both of Houston, Tex.

[73] Assignee: Baylor College of Medicine, Houston, Tex.

[21] Appl. No.: 09/071,876

[22] Filed: May 4, 1998

[51] Int. Cl.$^7$ ..................................................... C12Q 1/68
[52] U.S. Cl. .............................. 435/6; 536/26.6; 436/524
[58] Field of Search ................................ 435/6; 436/524; 536/26.6

[56] References Cited

U.S. PATENT DOCUMENTS

| | | | |
|---|---|---|---|
| 4,637,687 | 1/1987 | Haim et al. | 350/335 |
| 4,806,631 | 2/1989 | Carrico et al. | 536/27 |
| 4,818,681 | 4/1989 | Dattagupta | 435/6 |
| 4,826,789 | 5/1989 | Jones et al. | 501/8 |
| 4,826,790 | 5/1989 | Jones et al. | 501/80 |
| 4,937,188 | 6/1990 | Giese et al. | 435/41 |
| 4,957,858 | 9/1990 | Chu et al. | 435/6 |
| 4,963,436 | 10/1990 | Jones et al. | 428/403 |
| 5,008,220 | 4/1991 | Brown et al. | 501/81 |
| 5,024,933 | 6/1991 | Yang et al. | 435/6 |
| 5,055,429 | 10/1991 | James et al. | 501/80 |
| 5,190,864 | 3/1993 | Giese et al. | 435/41 |
| 5,215,882 | 6/1993 | Bahl et al. | 435/6 |
| 5,514,785 | 5/1996 | Van Ness et al. | 536/22.1 |
| 5,554,744 | 9/1996 | Bhongle et al. | 536/25.3 |
| 5,601,982 | 2/1997 | Sargent et al. | 435/6 |
| 5,610,287 | 3/1997 | Nikiforov et al. | 536/24.3 |
| 5,630,932 | 5/1997 | Lindsay et al. | 205/645 |
| 5,641,630 | 6/1997 | Snitman et al. | 435/6 |
| 5,807,756 | 9/1998 | Bauman et al. | 436/524 |

OTHER PUBLICATIONS

DeRisi, J., Penland, L., Brown, P.O., Bittner, M.L., Meltzer, P.S., Ray, M., Chen, Y., Su, Y.A., Trent, J.M., "Use of a cDNA microarray to analyse gene expression patterns in human cancer," Nature Genetics, 14:457–460 (1996).

Schena, M., Shalon, D., Davis, R.W., Brown, P.O., Science 270:467–470 (1995).

"Parallel human genome analysis: Microarray–based expression monitoring of 1000 genes," Schena, M., Shalon, D., Heller, R., Chai, A., Brown, P.O., Davis, R.W., "Quantitative Monitoring of Gene Expression Patterns with a Complementary DNA Microarray," Proc. Natl. Acad. Sci. USA, 93:10614–10619 (1996).

Shalon, D., Smith, S.J., Brown, P.O., "A DNA Microarray System for Analyzing Complex DNA Samples Using Two–color Fluorescent Probe Hybridization," Genome Research 6:639–645 (1996).

Maskos, U., Southern, E.M., "Oligonucleotide hybridisations on glass supports: a novel linker for oligonucleotide synthesis and hybridisation properties of oligonucleotides synthesised in situ," Nucleic Acids Research, 20:7 1679–1684 (1992).

Hacia, J.G., Brody, L.C., Chee, M.S., Fodor, S.P.A., Collins, F.S., "Detection of heterozygous mutations in BRCA1 using high density oligonucleotide arrays and two–color fluorescence analysis," Nature Genetics 14:441–447 (1996).

Lockhart, D.J., Dong, H., Byrne, M.C., Follettie, M.T., Gallo, M.V., Chee, M.S., Mittmann, M., Wang, C., Kobayoshi, M., Horton, H., Brown, E.L., "Expression monitoring by hybridization to high–density oligonucleotide arrays," Nature Biotechnology 14:1675–1680 (1996).

Guo, Z. Giufoyle, R.A., Thiel, A.J., Wang, R., and Smith, L.M., "Direct fluorescence analysis of genetic polymorphisms by hybridization with oligonucleotide arrays on glass supports", Nucleic Acids Research 22:24 5456–5465 (1994).

Ramsay, G., "DNA chips: State–of–the–art," Nature Biotechnology 16:40–44 (1998).

Marshall, A., and Hodgson, J., "DNA chips: An array of possibilities," Nature Biotechnology 16:27–31 (1998).

Castellino, A.M., "When the Chips are Down," Genome Research 7:943–946 (1997).

Schena, M., "Genome analysis with gene expression microarrays," 18:5 427–431 (1996).

Beattie, W.G., Meng, L., Turner, S.L., Varma, R.S., Dao, D.D., and Beattie, K.L., "Hybridization of DNA Targets to Glass–Tethered Oligonucleotide Probes," 4:213–225 (1995).

*Primary Examiner*—Scott W. Houtteman
*Attorney, Agent, or Firm*—Fulbright & Jaworski, L.L.P.

[57] ABSTRACT

The invention relates to novel chemically modified nucleic acids with enhanced lability towards solid supports, such as glass. These modified nucleic acids can be readily affixed to solid supports, for instance, a glass surface, without first derivatizing the glass surface. High-density microarrays based on these modified nucleic acids as well as methods for preparing these microarrays are also useful.

51 Claims, 6 Drawing Sheets

Top view

Side view

Where R is a linker, R1, R2 and R3 can be : -OCH$_3$, OC$_2$H$_5$, Cl; X=Cl, Br, or I

CHEMICALLY MODIFIED NUCLEIC ACIDS AND METHODS FOR COUPLING NUCLEIC ACIDS TO SOLID SUPPORT

BACKGROUND OF THE INVENTION

1. Technical Field of the Invention

The present Invention claims a closely related family of compounds, devices, and methods relating to techniques for immobilizing nucleic acids to a solid support for the purpose of conducting scientific investigation or routine testing upon the bound nucleic acid samples in areas such as genome-wide genetic mapping and gene expression studies.

2. The Prior Art

A large percentage of investigation in the biochemical arts is directed to studies involving nucleic acids, particularly deoxyribonucleic acid, or DNA. DNA is a water-soluble compound, that if left in solution (i.e., a water-based solution),is likely to degrade, through hydrolysis, and so forth. Obviously this frustrates any investigation involving DNA, and so therefore, accurate and reliable study involving DNA requires a method or device to ensure the integrity of DNA. To facilitate the study of DNA, it is often desirable to affix or immobilize the DNA on a solid surface, such as a smooth sheet of glass. Fixed in place in this manner, the DNA can be readily manipulated (i.e., reacted with other substances). If DNA is envisioned as a long strand, then immobilizing DNA means fixing one end of the strand to the solid support so that the remainder of the strand is unmodified and free to undergo further reaction depending upon the particular study. Indeed, this is a widely used method to conduct laboratory studies involving DNA.

Perhaps the major problem associated with immobilizing DNA on a solid support is exactly how to do it without altering the DNA (other than that relatively small portion that is actually bound to the solid support). This is a very difficult problem because whatever solid support is used must be essentially inert. That is, it must not react with the DNA, other than simply to immobilize it upon the solid support. Glass is a particularly suitable solid support, because it is inexpensive, and highly inert. At present, the current orthodoxy is that the solid support (e.g., a glass surface) must first be primed or derivatized so that it can bind one end of the DNA to the surface. Numerous techniques exist to do this.

Unfortunately, derivatizing the otherwise inert surface of glass creates problems which could confound the results of the laboratory study involving DNA. One problem is that derivatizing the glass surface creates a net positive electrostatic charge on the glass surface. Since DNA is (net) negatively charged, other DNA (or DNA used later in the study but not deliberately affixed to the glass surface) is prone to stick (by non-specific electrostatic attraction) to the glass surface. In other words, DNA "probes" which are single (rather than double) strands of DNA are often contacted with an array of DNA single strands affixed to a solid support. Since the probe has a known nucleotide sequence and since a particular single strand of DNA will bind preferentially to a complementary strand, the particular immobilized strand to which the probe reacts reveals the nucleotide sequence of the previously unknown immobilized strand. Yet simple experiments of this type (probe studies) are severely confounded by electrostatic sticking of the probe to the derivatized (hence electrostatically charged) glass surface. For instance, the probe is often radiolabeled so that its presence can be detected by an ordinary radiation detector. Thus, the location of the probe on the glass surface, as evidenced by the detector, reveals the chemical identity or sequence of the immobilized DNA strand at that particular location on the glass surface (which is known and designated in advance). Yet the radiation detector is unable to distinguish between probe that is chemically bound to a complementary strand of DNA affixed to the solid support, and probe that is simply electrostatically stuck to the glass surface (but not to a DNA strand).

Second, derivatized surfaces result in what shall be known as "spreading." Spreading occurs because the solid support surface becomes hydrophilic upon derivatization. As a result, when the DNA (desired to be immobilized upon the solid support) is contacted with the surface of the solid support, it spreads, rather than remaining in a discrete "spot," which it should ideally do, since whether the radioactive probe is detected in one spot or another determines whether the scientist infers that the probe reacted with this or that immobilized DNA. Spreading is a major constraint on array density (i.e., the number of different nucleic acid samples that can be arranged on a single solid support). Hence, any means to curtail spreading, and so increase array density, is highly desirable.

One very common substance used to prepare a glass surface to receive a nucleic acid sample is poly-L-lysine. See, e.g., DeRisi, et al., *Use of a cDNA Microarray to Analyze Gene Expression Pattern in Human Cancer*, 14 Nature Genetics 457 (1996); Shalon et al. in *A DNA Microarray System for Analyzing Complex DNA Samples Using Two-Color Fluorescent Probe Hybridization*, 6 Genome Res. 639 (1996); and Schena, et al., *Quantitative Monitoring of Gene Expression Patterns With a Complementary DNA Microarray*, 270 Science 467 (1995). Other types of pre-derivatized glass supports are commercially available (e.g., silylated microscope slides). See, e.g., Schena, et al., *Parallel Human Genome Analysis: Microarray-Based Expression Monitoring of 1000 Genes*, 93 P.N.A.S. 10614 (1996).

Numerous other surface coatings have been disclosed. See, e.g., U.S. Pat. No. 5,630,932, assigned to Molecular Imaging Corp., discloses a coating for a probe (platinum) tip for use in scanning tunneling microscopy; numerous means are disclosed for coating the surface, notably, $Si(OCH_3)$ $CH_2I$. U.S. Pat. No. 5,610,287, assigned to Molecular Tool, discloses coating a solid support with a salt or cationic detergent to non-covalently bond nucleic acids to the support. U.S. Pat. No. 5,024,933, assigned to Enzo Biochem, discloses coating a solid support with an isolate of naturally occurring mussel adhesive protein. U.S. Pat. No. 4,937,188, assigned to Northeastern University, discloses covalently bonding an enzyme to a solid support via molecular chain which acts as a substrate for the enzyme. U.S. Pat. No. 4,818,681, assigned to Molecular Diagnostics, discloses coating a solid support with a nucleoside phosphate through the heterocyclic moiety of the nucleoside; the nucleic acid is then immobilized upon the solid support by enzymatic coupling. U.S. Pat. No. 4,806,631, assigned to Miles, discloses activating a nylon solid support by partially solvolyzing the amine groups (e.g., by treating with an alkylating group) on the nylon surface.

Another approach to this problem involves derivatizing both the solid support and the nucleic acid sought to be immobilized. See, e.g., U.S. Pat. No. 5,641,630, assigned to Amgen and Abbott, discloses coating a solid support with a complexing agent that binds to an other complexing agent to which the nucleic acid sought to be bound is likewise bound. U.S. Pat. No. 5,554,744, assigned to Hybridon, discloses contacting a solid support with diisopropylcarbodiimide and an acid catalyst and a succinylated nucleoside to immobilize the nucleoside. U.S. Pat. No. 5,514,785, assigned to Becton Dickinson, discloses coating a solid support with, preferably, primary and secondary amines, followed by activation of the nucleic acid using cyanuric chloride. U.S. Pat. No. 5,215,882, assigned to Ortho Diagnostic Systems, discloses modifying the nucleic acid sought to be immobilized with a primary amine or equivalent, followed by reaction of the modified nucleic acid with the solid support (the support must have free aldehyde groups) in the presence of a reducing agent.

Finally, a third approach to the problem of immobilizing nucleic acids to solid support material involves creating a novel solid support. See, e.g., U.S. Pat. Nos. 5,055,429, 5,008,220, 4,963,436, 4,826,790, and 4,826,789, assigned to ECC International, disclose solid support material made from aluminosilicate material.

Due to the aforementioned shortcomings of derivatizing the (entire) glass surface prior to affixing the nucleic acid samples, several methods have been developed which involve synthesizing the nucleic acid samples directly to the solid support. See, e.g., Hacia, et al., Detection of Heterozygous Mutations in BRCA1 Using High Density Oligonucleotide Arrays and Two-Colour Fluorescence Analysis, 14 Nature Genetics 441 (1996); Lockhart, et al., Expression Monitoring by Hybridization to High-Density Oligonucleotide Arrays, 14 Nature Biotechnology 1675 (1996); Maskos and Southern, *Oligonucleotide Hybridizations on Glass Supports: a Novel Linker for Oligonucleotide Synthesis and Hybridization Properties of Oligonucleotides Synthesized In Situ*, 20 Nucleic Acids Res. 1679 (1992) (and references cited there, particularly 5–11).

To reiterate: at present, the prevailing view in the biochemical arts is that, in order to effectively immobilize nucleic acids onto solid surfaces, the solid support must first be derivatized, or made chemically labile, so that the nucleic acid can then be reacted with solid support. In addition, epoxides are known mutagens; that is, they are known to damage nucleic acids, particularly DNA.

Therefore, quite contrary to the current state of knowledge in the biochemical arts, the Invention presented here discloses and claims DNA (and nucleic acid more generally) that is modified such that they readily adhere to an unmodified or underivatized glass surface. In particular, the present Invention discloses and claims epoxide-modified nucleic acid (particularly DNA) which is readily affixed to an unmodified solid support.

SUMMARY OF THE INVENTION

One object of the present Invention is modified nucleic acid that will adhere to a solid surface to allow subsequent biochemical investigation.

Thus, in accordance with one aspect of the present Invention, a modified nucleic acid is claimed which comprises a nucleic acid covalently bound to moiety containing two crucial functional groups: a cyclic ether group and an alkoxysilane group. In accordance with other aspects of the present Invention, methods for preparing the aforementioned modified nucleic acids are claimed.

Also, in accordance with another aspect of the present invention, a high-density microarray is claimed which comprises a glass or other inert surface, made by printing numerous highly discrete modified DNA sample spots upon the surface.

In accordance with another aspect of the present Invention, another modified nucleic acid is claimed which is prepared from a nucleic acid and a halogenated silane.

In accordance with yet another aspect of the present Invention, another modified nucleic acid is claimed which is prepared by reaction of the nucleic acid with a brominated moiety, followed by reaction with an aminated silane.

In accordance with another aspect of the present Invention, a device is claimed which allows printing of the aforementioned high-density microarrays.

In accordance with yet another aspect of the present Invention, modified silanes are claimed which allow the skilled artisan to modulate the electrostatic properties of the solid surface to optimize sample density and detection sensitivity.

The present Invention possesses numerous advantages over the prior art. Many of the advantages derive from the fact that the solid surface, which is typically ordinary glass, remains highly chemically inert. Thus the previously mentioned problems of probe (or other reactant) sticking to the glass as well as "spreading" are entirely eliminated. The ultimate result is, among other things, far higher detection sensitivity compared with state-of-the-art derivatized solid support.

In addition, the nucleic acid to be immobilized upon the solid support is readily derivatized. The reaction of the epoxide derivatives of the present Invention is simply to execute-it occurs under mild conditions, reaction rates are quick, and equilibrium is highly favorable. Moreover, the epoxide-modified nucleic acid of the present Invention is essentially permanently stable, thus it can be prepared and stored for later use. Additional, more specific advantages will be disclosed later during discussion of particular embodiments of the present Invention.

Other and further objects, features, and advantages will be apparent from the following description of the presently preferred embodiments of the invention, which are given for the purpose of disclosure, when taken in conjunction with the accompanying drawings.

Figure 1:
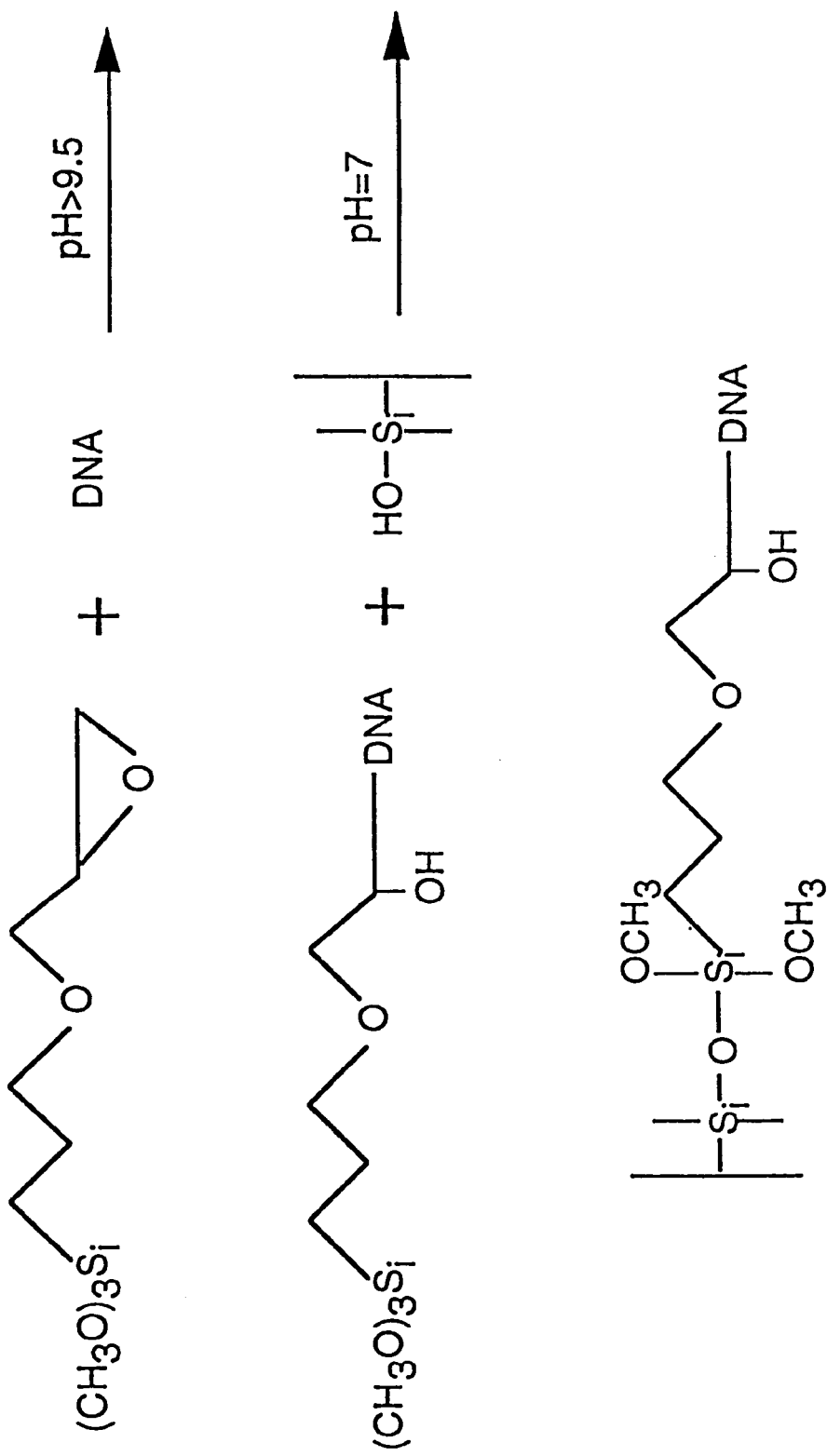
FIG. 1 depicts a coupling reaction of nucleic acid (in this instance DNA) with 3-glycidoxypropyltrimethoxysilane, followed by the reaction of the newly modified DNA and the solid support (in this instance a glass surface). The final reaction product—the immobilized DNA is shown at bottom.

Drawings are not necessary to scale. Certain features of the invention may be exaggerated in scale or shown in schematic form in the interest of clarity and conciseness.

DETAILED DESCRIPTION OF THE PREFERRED EMBODIMENTS

It will be readily apparent to one skilled in the art that various substitutions and modifications may be made to the invention disclosed herein without departing from the scope and spirit of the invention.

The gist of this invention is chemical modification of the nucleic acid sought to be immobilized. This chemically modified nucleic acid is then readily reacted to a solid support such as a glass surface, rendering the nucleic acid immobilized. Again, this is in direct contradiction to the prior art, which teaches modification of the solid support, rather than the nucleic acid itself.

The modified nucleic acids of the present Invention readily adhere to a variety of solid surfaces having hydroxyl groups. These include, though are not limited to: quartz glass, mica, alumina ($Al_2O_3$), titania ($TiO_2$), $SnO_2$, $RuO_2$, $PtO_2$, as well as numerous other metal oxide surfaces.

In one family of embodiments, the chemically modified nucleic acids of the present Invention are so modified with compounds having two crucial functionalities: a ring ether and an alkoxysilane group. The nucleic acid reacts with the ring ether, then the newly modified nucleic acid is contacted with the otherwise inert glass surface, where the alkoxysilane group reacts with the Si—OH groups on the glass surface.

In another distinct family of embodiments, the chemically modified nucleic acids of the present Invention are so modified with compounds having two crucial functionalities: an amino group and an alkoxysilane group. The nucleic acid reacts with the amino group, then the newly modified nucleic acid is contacted with the otherwise inert glass surface, where the alkoxysilane group reacts with the Si—OH groups on the glass surface.

In yet another distinct family of embodiments, the nucleic acids are modified by reaction with halogenated silane compounds. In a fourth set of embodiments, the nucleic acids are derivatized by a two-step process involving a final reaction with amine-containing silanes and brominated nucleic acids.

Other embodiments are directed to preparing and optimizing high-density microarrays utilizing the modified nucleic acids of the prior embodiments of the present Invention.

EXAMPLE 1

Preparation of Modified Nucleic Acid Using 3-glycidoxypropyltrimethoxysilane

This example describes one form of modified nucleic acid of the present Invention. The purpose of the chemical modification is to enable the nucleic acid to be readily affixed to an underivatized solid surface. In this example, the nucleic acid—preferably DNA—is modified by reaction with 3-glycidoxypropyltrimethoxysilane (GPTS), according to FIG. 1. GPTS has in fact been previously used to derivatize a glass surface upon which (unmodified) DNA samples are then contacted and immobilized. Yet the use of GPTS is for the opposite purpose: to modify the DNA for subsequent attachment to an underivatized glass surface has not been previously disclosed nor suggested. Moreover, GPTS—since it contains an epoxide group—is known to damage DNA in vivo. For these reasons, its use to derivatize DNA is actually discouraged by the prior art.

Schematically, affixing the nucleic acid to the solid support consists essentially of two steps. In the first, the nucleic acid reacts with the epoxide end of the GPTS molecule; in the second step, the glass surface reacts with the other end, or the silane end of the GPTS-modified nucleic acid, thereby affixing the nucleic acid onto an underivatized glass surface. The entire reaction is rapid, is characterized by a favorable equilibrium, and occurs under very mild conditions using a minimum of inexpensive reagents. Though there quite obviously are numerous ways to carry out either step of the reaction, the preferred method is shown in this and the following example.

As depicted in FIG. 1, a chemical compound having a cyclic or ring ether and an alkoxysilane—in this instance ethylene oxide and trimethyloxysilane, respectively—comprise the two ends of the compound; the two ends are connected by a four-carbon ether linkage. The compound shown is 3-glycidoxypropyltrimethoxysilane or GPTS. In the first step, DNA is reacted with GPTS at basic pH, preferably above 9.5, to form the modified DNA. The modified DNA is then reacted with an underivatized glass (or other silanol-containing) surface at neutral pH, thus immobilizing the DNA onto the glass surface. In the first step, the ring ether functionality reacts with the DNA. Again, the ring ether need not be ethylene oxide, as it is in GPTS, although the small ring is preferred to increase reactivity of the ether functionality which is relatively unreactive.

The first reaction, leading to the derivatized DNA, is a ring-opening reaction likely involving carbon 5 of the ribose ring of the DNA. This derivatized DNA is unusually stable and can be stored for long periods of time prior to actual use. The second reaction, immobilizing the derivatized DNA onto the glass surface, is a simple substitution reaction creating an Si—O—Si linkage in the glass surface, and removing one of the alkoxy groups from the GPTS molecule.

EXAMPLE 2

Preparation of Modified Nucleic Acid Using 3-aminopropyltriethoxysilane

This example describes another preferred form of modified nucleic acid of the present Invention. The purpose of the chemical modification is to enable the nucleic acid to be readily affixed to an underivatized solid surface. In this example, the nucleic acid, preferably DNA, is modified by reaction with 3-aminopropyltrimethoxysilane, according to FIG. 2. As in example 1, affixing the nucleic acid to the solid support consists essentially of two steps. In the first, the nucleic acid reacts with the amino end of the 3-aminopropyltrimethoxysilane molecule; in the second step, the glass surface reacts with the other end, or the silane end of the 3-aminopropyltrimethoxysilane-modified nucleic acid, thereby affixing the nucleic acid onto an underivatized glass surface.

As in example 1, the entire reaction is rapid, is characterized by a favorable equilibrium, and occurs under very mild conditions using a minimum of inexpensive reagents. Though there quite obviously are numerous ways to carry out either step of the reaction, the preferred method is shown in this and the following example.

Figure 2:
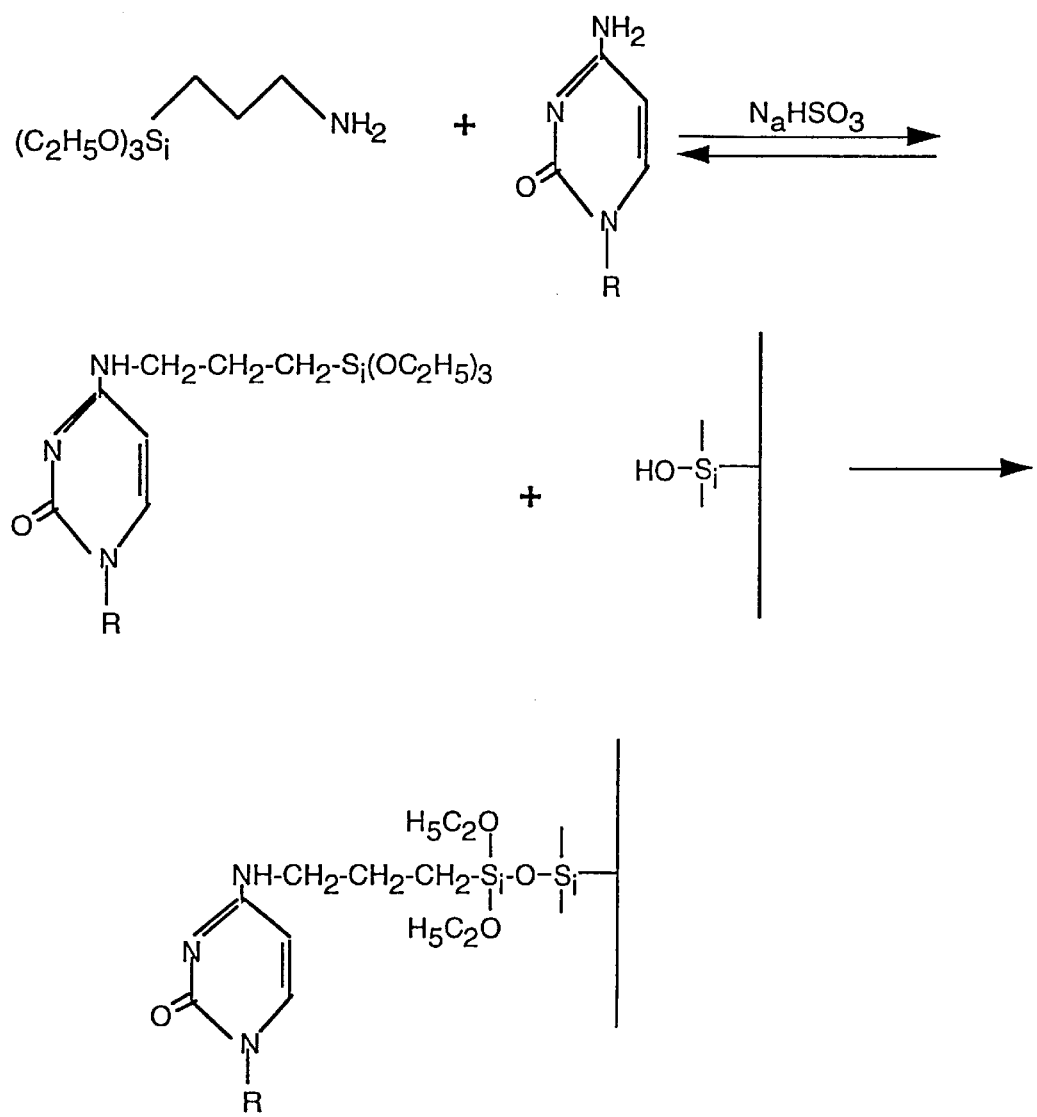
FIG. 2 depicts a coupling reaction of nucleic acid (in this instance DNA) with 3-aminoproplytriethoxysilane followed by the reaction of the newly modified DNA and the solid support (in this instance a glass surface) The final reaction product-the immobilized DNA is shown at bottom.

As depicted in FIG. 2, a chemical compound having an amino group and an alkoxysilane—in this instance —$NH_2$ and triethyloxysilane, respectively-comprise the two ends of the compound; the two ends are connected by a propyl linkage. The compound shown is 3-aminopropyltriethoxysilane. In the first step, DNA is reacted with 3-aminopropyltriethoxysilane at neutral pH in the presence of preferably sodium bisulfite.

The first reaction, leading to the derivatized DNA, is transamination reaction of the cytosine residues on nucleic acids. The second reaction as in Example 1, immobilizing the derivatized DNA onto the glass surface is a simple substitution reaction creating an Si—O—Si linkage in the glass surface, and removing one of the alkoxy groups from the GPTS molecule.

EXAMPLE 3

Preparation of a High-Density Microarray

Once the modified nucleic acids of the present Invention, such as those described in Examples 1 and 2, are prepared, they can then be exploited. Again, these modified nucleic acids (particularly DNA) can be immobilized onto a glass surface simply by contacting the modified DNA onto the underivatized surface. The significance of this is, among other things, that spreading (migration of the DNA sought to be immobilized from the desired location) and non-specific probe sticking (caused by derivatization of the glass surface which creates a net positive electrostatic charge upon the surface which attracts the net negatively charged DNA) are essentially eliminated.

These advantages allow the creation of extraordinarily high-density microarrays, which is highly desirable. For instance, due to the elimination of spreading, and the effective elimination of probe sticking, a single small glass surface can contain virtually thousands of DNA samples to be tested, each of which is microscopic in size, all immobilized upon a single glass surface. Indeed, one can construct a microarray consisting of multiple single sample spots smaller than 50 microns placed upon a glass surface.

Figure 3A:
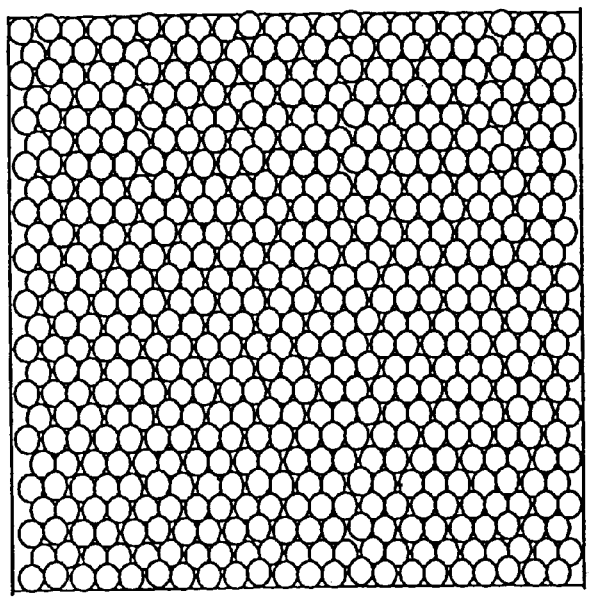
FIG. 3 depicts a device for making a high-density microarray; both a top (FIG. 3A) and a side view (FIG. 3B) are shown.
Figure 3B:
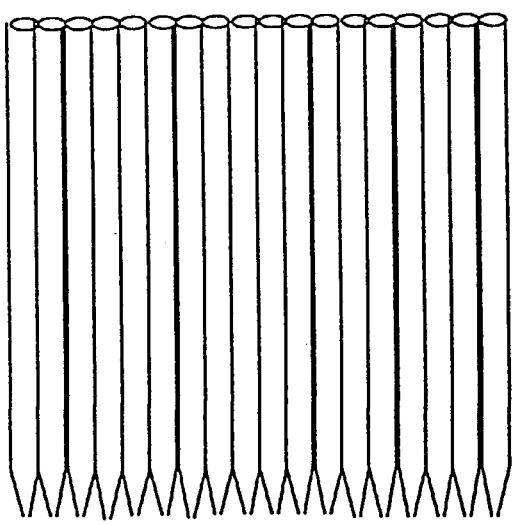

A high-density microarray consisting of multiple DNA samples of this type is also easily constructed in accordance with the present Invention. The modified DNA can be prepared (for instance, in accordance with Examples 1 and 2) well in advance of actual use. These chemically modified DNA samples are analogous to "DNA chips" that can then be readily "imprinted" upon an unaltered glass sheet in, for instance, grid fashion. FIG. 3 illustrates one embodiment of a device for preparing such a high-density microarray using the DNA chips of the present Invention. In one preferred embodiment, the device is made from a plurality of inexpensive commercially available capillary micropipets, preferably 10 cm micropipets, although other sizes will, of course, work. As depicted in FIG. 3 each 10 cm micropipet is pulled to make a taper at one end. They are arranged in a hexagonal close-packed array, bounded by a square frame. The micropipets can be glued to one another to form a stable unit within the frame. The tapered ends (FIG. 3B) are cut off and polished to optical flatness.

To prepare the microarray, the tips of the device are dipped into a multi-well container which contains the (chemically modified in accordance with the present Invention) DNA samples to be tested, and whose wells are aligned with the micropipets of the device. Upon contact of the tips into the wells, a small portion of each DNA sample is deposited into the micropipet corresponding to the particular well by simple capillary action. The size of the spot can be carefully controlled by the size of the tapered end. Using this device and the DNA chips of the present Invention, thousands of samples can be arrayed in a narrow area, simultaneously and without the need for expensive robotics. Indeed, the method (comprising the DNA chips and pipet device) of the present Invention has been shown to be even more efficient than methods using high-speed spotting robots. Finally, the compounds, methods and devices of the present Invention are readily incorporated into a pre-packaged kit for commercial sale.

The high-density microarray of the present Invention can also be readily incorporated into the microarray systems of the prior art, such as those disclosed in the prior art section above. These methods are hereby incorporated by reference into the present Application, for instance, fluorescent in situ hybridization (FISH) and the method described in Shalon, et al. in *A DNA Microarray System for Analyzing Complex DNA Samples Using Two-Color Fluorescent Probe Hybridization,* 6 Genome Res. 639 (1996). In the Shalon, et al. method, a microarray system is presented for analyzing DNA samples that involves making microarrays of DNA samples on glass substrates, probing them by hybridization with complex fluorescent-labeled probes, and using a laser-scanning microscope to detect the fluorescent signals representing hybridization. Similarly, Sargent, et al. (U.S. Pat. No. 5,601,982) discloses a method and apparatus for determining the sequence of polynucleotides involving scanning the nucleic acids by scanning tunneling microscopy.

EXAMPLE 4

Preparation of Modified Nucleic Acids Using Halogenated Silanes

Figure 4:
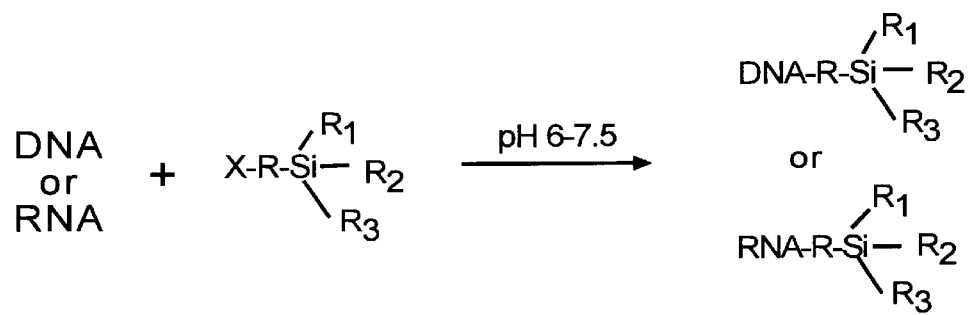
FIG. 4 depicts the silanization of nucleic acid through alkylation of halogen-containing silane compounds.

This example describes another form of modified nucleic acid of the present Invention. Again, the purpose of the chemical modification disclosed and claimed here is to enable to nucleic acid to be readily affixed to an underivatized solid surface, e.g., ordinary quartz glass. According to FIG. 4, a modified nucleic acid in accordance with the present Invention is prepared by reacting unmodified nucleic acid under near neutral pH with suitable silane compounds. The "X" in FIG. 4 can refer to any halide, preferably Cl, Br, or I; $R_1$, $R_2$ and $R_3$, can be the same or different, including, —$OCH_3$, and —$OC_2H_5$. In particularly, preferred embodiments, the halogenated silane depicted to the left of the arrow in FIG. 4 is 8-bromocytltrichlorosilane, 8-bromocytltrimethoxysilane, 4-chlorobutylmethyldichlorosilane, and 3-iodopropyltrimethoxysilane.

The conversion depicted in FIG. 4 was performed as follows. The halogenated silane was dissolved in dimethyl-formamide (DMF) at a concentration of about 30 mM. Next, 3 to 10 ug of nucleic acid was dissolved in 100 ul of 0.01 M phosphate buffer (pH 7.0). Then 1 to 3 ug of 30 mM halogenated silane was added, the solution is then mixed well, and allowed to react at about 37 C. for about 3 hours (alternatively, it can be reacted at ambient temperature overnight). After reaction, the desired product—the modified nucleic acid—is purified by ethanol precipitation; then the modified nucleic acid is dissolved in water.

EXAMPLE 5

Controlling Spot Density/Size

As discussed throughout the present Application, one particular advantage of the present Invention is that it allows the investigator to prepare unusually high-density microarrays to conduct nucleic acid studies. This example is best understood in relation to example 3 which disclosed the preparation of a high-density microarray in accordance with the present Invention. This example discloses enhanced methods for controlling the size of the individual nucleic acid "spots" on the solid supports, in accordance with the present Invention.

Small spot size, in relation to high-density microarrays, allows higher sample density (i.e., more samples per unit area) and superior detection sensitivity (because the signals are less diffuse). In the conventional solid support systems, the skilled artisan faces a crucial dilemma. An ordinary clean quartz glass surface—of the type used in the experiments described here—is very hydrophilic. Thus, nucleic acid samples will naturally tend to spread out when placed on the glass surface. Again, this is undesirable. To mitigate spreading, the skilled artisan can treat the surface to make it more hydrophobic—e.g., either pretreating the surface with a hydrophobic agent, or simply by dehydrating the surface. Naturally, either of these options makes the glass surface less reactive towards silane-modified nucleic acids.

Figure 6:
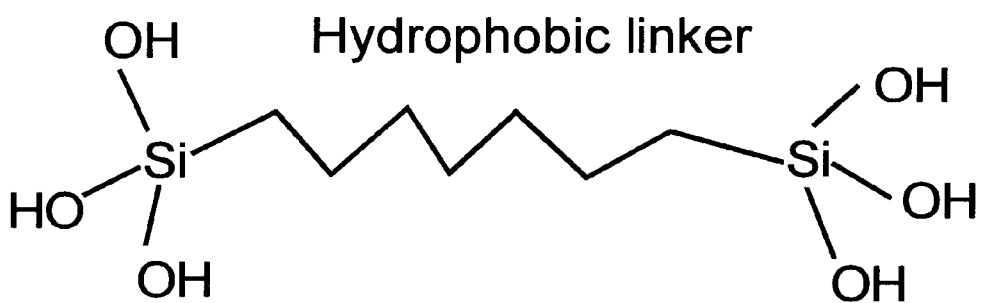
FIG. 6 is a schematic representation of one embodiment of the present Invention showing silane linkers by hydrophobic linkers.

In a family of embodiments of the present Invention discussed in this example, the skilled artisan is spared this dilemma. More specifically, spreading can be eliminated yet the reactivity of the surface towards the modified nucleic acids can be maintained through the use of another type of silanes of the present Invention. For instance, one quite general embodiment of these silanes after hydrolysis contains an $Si(OH)_3$ at each end, linked by a hydrophobic group. See FIG. 6. Any of a variety of hydrophobic linkers can be used. Particularly preferred embodiments include: 1,6-Bis-trichlorosilyhexane, 1,8-Bis-trichlorosilyloctane, 1,6-Bis-trimethoxysilyhexane, and 1,4 Bis-trimethoxysilylethylbenzene. Thus, according to these embodiments of the present Invention, one end of the silane attaches to the surface, and the other end remains reactive to the modified nucleic acids. The hydrophobic linker confers hydrophobicity to the surface. Thus, the skilled artisan can readily see how the electrostatic properties of the surface (hydrophobic versus hydrophilic) can be readily modulated—e.g., the chain length of the linker can be adjusted to control hydrophobicity, and the surface reactivity can be controlled by adjusting the amount of silane contacted with the surface.

To prepare the solid supports in accordance with this aspect of the present Invention, the glass surface was cleaned by slowly boiling in 3 M HCl for about 2 hrs in a fume hood. Next, the surfaces were rinsed with deionized water then kept in 0.1 M HCl until ready for use. When ready for use, the surfaces were rinsed with doubly distilled deionized water to remove any extant acid, then rinsed in absolute ethanol. Next, the surfaces were immediately transferred to an ethanol solution containing 0.0005 % to 0.002 % of the bi-functional silanes of this aspect of the Invention. The surfaces were then treated at room temperature for about 48 hours. The surfaces were then rinsed with ethanol and air dried. Finally, the glass surfaces were stored in a dust-free environment until ready for use.

EXAMPLE 6

Preparation of Modified Nucleic Acid Using Amine-Containing Silane Compounds

Figure 5A:
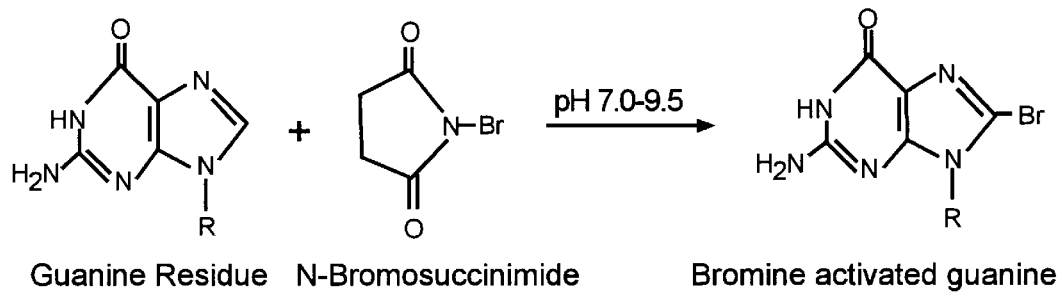
FIG. 5a depicts the first step in the silanization of nucleic acid using amine-containing silane compounds. In this case, the reaction occurs preferentially at the guanine base at neutral and slightly basic pH.
Figure 5B:
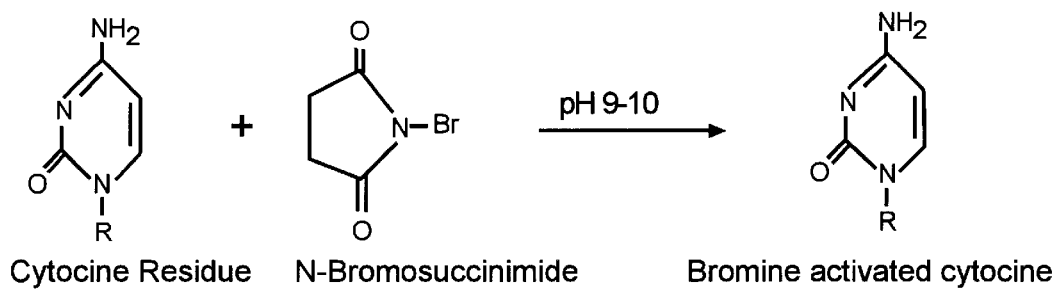
FIG. 5b depicts the first step in the silanization of nucleic acid using amine-containing silane compounds. In this case, the reaction occurs preferentially at the cytosine base at more basic pH.
Figure 5C:
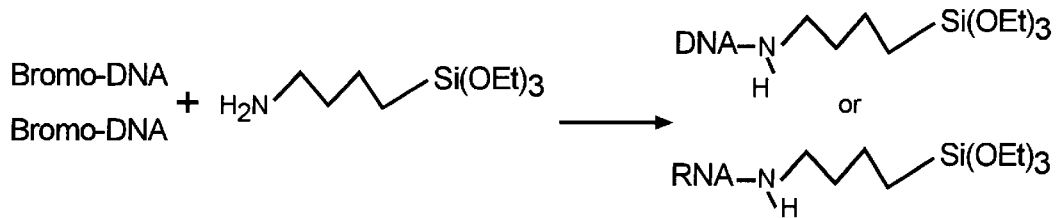
FIG. 5c depicts the second and final step in the silanization of nucleic acid using amine-containing silane compounds.

This example describes another form of modified nucleic acid of the present Invention. In this family of embodiments, the modified nucleic acid is prepared by reacting pristine nucleic acids with an amine-containing silane. Heuristically, the derivatization of nucleic acid with amine-containing silanes is comprised of two steps: (1) the halogenation (or bromination, as shown) of the nucleic acid (FIG. 5a, 5b); and (2) the derivatization of the halogenated nucleic acid (FIG. 5c). As depicted in FIG. 5a, 5b, the reaction can occur in the presence of N-bromosuccinimide under mild pH conditions; varying either of these reaction variables allows the skilled biochemist to control the reaction rate. Also as evidenced by FIG. 5a, 5b, the reaction normally occurs at the guanine or cytosine base depending upon the pH—i.e., neutral to slightly basic pH favors reaction at the guanine residue, more basic pH favors reaction at the cytosine residue.

Slightly different reaction protocols are preferably used depending upon whether the nucleic acid is DNA or RNA. For DNA, 5 ug of DNA was dissolved in 100 ul of 0.1 M $NaHCO_3$, to reach a pH of about 9.5. This solution is kept on ice for about 5 minutes. Contemporaneously, a fresh N-bromosuccinimide solution at concentration of about 10 mM was prepared and also chilled on ice. Next, 1 ul of the N-bromosuccinimide solution is added to the DNA solution; the solution was then stirred vigorously (to vortex). The reaction was then allowed to proceed on ice for about 15 minutes. Next, 10 ul of 0.5 M aminosilane solution at pH about 9.5–12, was added to the bromine-activated DNA solution; this new mixture was allowed to react at 65 C for about 2 hours. Finally, the silane-modified DNA was purified by methods well known in the art; preferably, it is purified by ethanol precipitation.

A similar, though slightly different protocol was used, 5 ug of RNA was dissolved in 100 ul of 0.1 M phosphate buffer, to reach a pH of about 7.5. This solution is kept on ice for about 5 minutes. Contemporaneously, a fresh N-bromosuccinimide solution at concentration of about 10 mM was prepared and also chilled on ice. Next, 1 ul of the N-bromosuccinimide solution is added to the DNA solution; the solution was then stirred vigorously (to vortex). The reaction was then allowed to proceed on ice for about 15 minutes. Next, 10 ul of 1 M aminosilane solution at pH about 8.0, was added to the bromine-activated DNA solution; this new mixture was allowed to react at 45 C. for about 2 hours. Finally, the silane-modified DNA was purified by methods well known in the art; preferably, it is purified by ethanol precipitation.

In these embodiments the following silanes are available for these reasons:

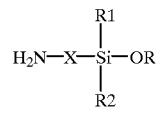

R: —$CH_3$, $C_2H_5$; R1: H,—$CH_3$,—$C_2H_5$,—$OCH_3$,—$OC_2H_5$
R2: H,—$CH_3$,—$C_2H_5$,—$OCH_3$,—$OC_2H_5$
X: a linker Further any other amino silane compound after hydrolysis that takes the following form is useful:

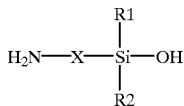

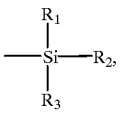

All patents, publications mentioned in this specification are indicative of the level of those skilled in the art to which the invention pertains. All patents, publications herein are incorporated by reference to the same extent as if each individual publication was specifically and individually indicated to be incorporated by reference.

One skilled in the art will readily appreciate that the present invention is well adapted to carry out the objects and obtain the ends and advantages mentioned as well as those inherent therein. The chemically modified nucleic acids, their attachment to solid support, along with the sequences, methods, procedures, assays, molecules, devices and specific compounds described herein are presently representative of the preferred embodiments are exemplary and are not intended as limitations on the scope of the invention. Changes therein and other uses will occur to those skilled in the art which are encompassed within the spirit of the invention and are defined by the scope of the claims.

What is claimed is:

1. A modified nucleic acid comprising a nucleic acid covalently bound to a compound having the formula:

wherein $R_1$ is an epoxide group;

wherein $R_2$ is an alkoxysilane group; and wherein X is moiety, chemically suitable for linking said epoxide group and said alkoxysilane group.

2. The modified nucleic acid of claim 1 wherein said epoxide group is ethylene oxide.

3. The modified nucleic acid of claim 1 wherein said alkoxysilane is selected from the group consisting of —Si(OCH$_3$)$_3$, —Si(OC$_2$H$_5$)$_3$, —Si(OCH$_3$)H$_2$, —SI(OCH$_3$)(CH$_3$)$_2$, and —Si(OCH)$_3$)$_2$CH$_3$.

4. The modified nucleic acid of claim 1 wherein said compound is 3-glycidoxypropyltrimethoxysilane.

5. The modified nucleic acid of claim 1 wherein said nucleic acid is DNA.

6. The modified nucleic acid of claim 1 wherein said nucleic acid is RNA.

7. A modified nucleic acid comprising a nucleic acid covalently bound to a compound having the formula:

wherein $R_1$ is an amino group;

wherein $R_2$ is an alkoxysilane group; and wherein X is moiety, chemically suitable for linking said amino group and said alkoxysilane group.

8. The modified nucleic acid of claim 7 wherein said amino group is a primary amine.

9. The modified nucleic acid of claim 7 wherein said alkoxysilane is selected from the group consisting of —Si(OCH$_3$)$_3$, —Si(OC$_2$H$_5$)$_3$, and wherein $R_1$, $R_2$, and $R_3$ are selected from the group consisting of —H, —CH$_3$, —OCH$_3$, and —OC$_2$H$_3$, and provided that at least one of $R_1$, $R_2$, or $R_3$ is either —OCH$_3$, or —OC$_2$H$_3$.

10. The modified nucleic acid of claim 7 wherein said compound is 3-aminopropyltriethoxysilane.

11. The modified nucleic acid of claim 7 wherein said nucleic acid is DNA.

12. The modified nucleic acid of claim 7 wherein said nucleic acid is RNA.

13. The modified nucleic acid of claim 7 wherein said nucleic acid contains a cytosine residue.

14. A device for making high-density microarrays comprising a plurality of capillary micropipets, having a distal and a tapered proximal end, wherein said micropipets are:

arranged equatorially in a substantially close-packed arrangement; and tapered at each said proximal end and wherein said ends are essentially planar.

15. The device of claim 14 wherein said micropipets are arranged in a close-packed square arrangement.

16. The device of claim 14 wherein said micropipets are bound by a frame.

17. The device of claim 16 wherein said micropipets are affixed to a base.

18. A high-density microarray comprising:

a solid support;

modified nucleic acid prepared by reacting said nucleic acid with an alkoxysilane selected from the group consisting of 3-glycidoxypropyltrimethoxysilane and 3-aminopropyltriethoxysilane, and immobilized about said solid support in orderly discrete spots.

19. The high-density microarray of claim 18 wherein said solid support is glass.

20. The high-density microarray of claim 18 wherein said discrete spots are about 50 microns in diameter.

21. A high-density microarray comprising:

the modified nucleic acid of claim 18;

a solid support upon which said plurality of closely spaced samples of said modified nucleic acid samples are placed.

22. The high-density microarray of claim 18 wherein said samples are placed upon said solid support using a device for making high-density microarrays.

23. A high-density microarray comprising a solid support having a plurality of modified silane moieties affixed, wherein said silane moieties are selected from the group consisting of —Si—(CH$_2$)$_n$—, wherein n=3, 4, 5, 6, 7, 8, or 9; and —Si—CH$_2$—CH$_2$—C$_6$H$_4$—CH$_2$—CH$_2$—Si—.

24. A method for modulating the electrostatic properties of a glass solid support comprising selectively reacting said solid support with silanes selected from the group consisting of: 1,6-Bis-trichlorosilylhexane, 1,8-Bis-trichlorosilyloctane, 1,6-Bis-trimethoxysilylhexane, and 1,4-Bis-trimethyloxysilylethylbenzene.

25. A modified nucleic acid prepared by:

reacting a guanine or cytosine base of said nucleic acid with N-bromosuccinimide at pH about 8.0 to form a brominated nucleic acid;

reacting said brominated nucleic acid with a silane having the formula $H_2N-(CH_2)_n-Si(OC_2H_5)_3$, wherein n=3, 4, 5, 6, 7, 8, or 9.

26. A modified nucleic acid comprising a nucleic acid covalently bound to a compound having the formula:

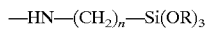

wherein n=3, 4, 5, 6, 7, 8, or 9.

27. The modified nucleic acid of claim 26 wherein R is selected from the group consisting of $-CH_3$, $-C_2H_5$, and $C_3H_7$.

28. A modified nucleic acid comprising a nucleic acid covalently bonded to a compound having the formula:

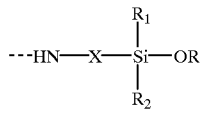

wherein R is selected from the group consisting of $-CH_3$, $-C_2H_5$, and $-C_3H_7$;

wherein $R_1$ and $R_2$ are the same or different and are selected from the group consisting of $-H$, $-CH_3$, $-C_2H_5$, $-OCH_3$, $-OC_2H_5$, $-C_3H_7$, and $-OC_3H_7$; and wherein X linking group comprising an at least partially aliphatic chain.

29. A method for immobilizing nucleic acid to solid support comprising:

reacting a compound of the formula $R_1-X-R_2$ with a nucleic acid to form a derivatized nucleic acid; wherein $R_1$ is an epoxide group; wherein $R_2$ is an alkoxysilane group; and, wherein X is a moiety chemically suitable for linking said epoxide group and said alkoxysilane group; and, reacting said derivatized nucleic acid with said solid support.

30. The method of claim 29 wherein said compound is 3-glycidoxypropyltrimethoxysilane.

31. A method for immobilizing nucleic acid to solid support comprising:

reacting compound of the formula $R_1-X-R_2$ with a nucleic acid to form a derivatized nucleic acid; wherein $R_1$ is an amino group; wherein $R_2$ is an alkoxysilane group; and, wherein X is a moiety chemically suitable for linking said amino group and said alkoxysilane group; and reacting said derivatized nucleic acid with said solid support.

32. The method of claim 31 wherein said compound is 3-aminopropyltriethoxysilane.

33. A modified nucleic acid comprising a nucleic acid covalently bound to a compound having the formula:

wherein $R_1$ is a cyclic ether;

wherein $R_2$ is $-NR_4$, wherein each $R_3$ group are the same or different alkyl groups, and $R_4$ is $-H$ or an alkyl group; and wherein X is moiety, chemically suitable for linking said cyclic ether group and said alkoxysilane group.

34. A modified nucleic acid comprising a nucleic acid covalently boded to a compound having the formula:

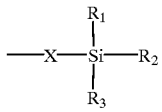

wherein $R_1$, $R_2$, and $R_3$, are the same or different, and are selected from the group consisting of $-OCH_3$, $-OC_2H_5$, $-OC_3H_7$, and $-Cl$; and wherein X is a moiety, chemically suitable for linking said nucleic acid to said compound.

35. The method of claim 29 or 30 wherein said nucleic acid is DNA.

36. The method of claim 29 or 30 wherein said nucleic acid is RNA.

37. The method of claim 29 or 30 wherein said first reacting step occurs at basic pH.

38. The method of claim 35 wherein said first reacting step occurs at pH from about 6 to about 12.

39. The method of claim 36 wherein said first reacting step occurs at pH from about 6 to about 8.5.

40. The method of claim 37 wherein said pH is greater than 9.5.

41. The method of claim 29 or 30 wherein said solid support is glass.

42. The method of claim 29 or 30 wherein said second reacting step occurs at approximately neutral pH.

43. The method of claim 31 or 32 wherein said nucleic acid is DNA.

44. The method of claim 31 or 32 wherein said nucleic acid is RNA.

45. The method of claim 31 or 32 wherein said nucleic acid contains a cytosine residue.

46. The method of claim 31 or 32 wherein said first reacting step occurs at essentially neutral pH.

47. The method of claim 44 wherein said first reacting step occurs at about pH=6.0–7.0.

48. The method of claim 31 or 32 wherein said first reacting step occurs in the presence of sodium bisulfite.

49. The method of claim 31 or 32 wherein said solid support is glass.

50. A kit for performing a hybridization assay on nucleic acid samples comprising:

a solid support; and a device for imprinting an array of DNA chips of modified nucleic acids of claim 1, 7, 25, 28, or 34 onto said solid support.

51. The modified nucleic acid of claim 33 wherein said compound selected from the group consisting of $-(CH_2)_8SiCl_3$, $-(CH_2)_8Si(OCH_3)_3$, $-(CH_2)_4SiCl_2CH_3$, and $-CH_2CH_2CH_2Si(OCH_3)_3$.

* * * * *

UNITED STATES PATENT AND TRADEMARK OFFICE
CERTIFICATE OF CORRECTION

PATENT NO.    : 6,048,695  
DATED         : April 11, 2000  
INVENTOR(S)   : Allan Bradley and Wei Wen Cai It is certified that error appears in the above-identified patent and that said Letters Patent is hereby corrected as shown below:

Drawings,  
Sheet 5, Figure 5b, "Cytocine" should read -- Cytosine --.

Column 8,  
Line 47, "8-bromocytltrchlorosilane" should read -- 8-bromocytyltrichlorosilane --.  
Line 48, "8-bromocytltrimethoxysilane" should read  
-- 8- bromocytyltrimethoxysilane --.

Column 11,  
Line 44, "—SI(OCH$_3$)" should read -- —Si(OCH$_3$) --.

Column 12,  
Line 9, "—OC$_2$H$_3$" should read -- —OC$_2$H$_5$ --.  
Line 11, "—OC$_2$H$_3$" should read -- OC$_2$H$_5$ --.

Column 13,  
Lines 60-61, "wherein each R$_3$ group are the same or different alkyl groups," should be deleted.

Signed and Sealed this

Seventeenth Day of February, 2004

JON W. DUDAS  
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 6,048,695 | Page 1 of 1 |
| APPLICATION NO. | : 09/071876 | |
| DATED | : April 11, 2000 | |
| INVENTOR(S) | : Allan Bradley and Wei-Wen Cai | |

It is certified that error appears in the above-identified patent and that said Letters Patent is hereby corrected as shown below:

At Column 1, after the title and before the section entitled "BACKGROUND OF THE INVENTION," please insert the following sentences:

Certain embodiments disclosed herein were made with Government support under a grant from the National Institutes of Health, No. R21 CA83211. The Government may have certain rights.

Signed and Sealed this

Thirtieth Day of January, 2007

JON W. DUDAS
*Director of the United States Patent and Trademark Office*